United States Patent [19]

Knight et al.

[11] Patent Number: 5,229,510

[45] Date of Patent: * Jul. 20, 1993

[54] β-LACTAMS USEFUL IN DETERMINING THE AMOUNT OF ELASTASE IN A CLINICAL SAMPLE

[75] Inventors: Wilson B. Knight, Watchung; William K. Hagmann, Westfield, both of N.J.; Alan L. Maycock, Malvern, Pa.

[73] Assignee: Merck & Co., Inc., Rahway, N.J.

[*] Notice: The portion of the term of this patent subsequent to Jan. 3, 2009 has been disclaimed.

[21] Appl. No.: 816,982

[22] Filed: Jan. 3, 1992

Related U.S. Application Data

[63] Continuation-in-part of Ser. No. 761,191, Sep. 20, 1991, which is a continuation-in-part of Ser. No. 719,653, Jun. 12, 1991, abandoned, and a continuation-in-part of Ser. No. 735,696, Jul. 25, 1991, abandoned, said Ser. No. 719,653, is a continuation of Ser. No. 608,607, Oct. 31, 1990, abandoned, which is a continuation of Ser. No. 388,771, Aug. 2, 1989, abandoned, which is a continuation-in-part of Ser. No. 179,688, Apr. 11, 1988, abandoned, which is a continuation-in-part of Ser. No. 89,797, Aug. 27, 1987, abandoned, which is a continuation of Ser. No. 842,834, Mar. 27, 1986, abandoned, which is a continuation-in-part of Ser. No. 721,811, Apr. 10, 1985, Pat. No. 4,680,391, which is a continuation-in-part of Ser. No. 557,030, Dec. 1, 1983, abandoned, said Ser. No. 735,696, is a continuation of Ser. No. 597,617, Oct. 15, 1990, abandoned.

[51] Int. Cl.$^5$ .............. C07D 205/08; C07D 405/12; C07D 413/12; A61K 31/395
[52] U.S. Cl. .............................................. 540/360
[58] Field of Search ........................................ 540/360

[56] References Cited

U.S. PATENT DOCUMENTS

| | | | |
|---|---|---|---|
| 4,064,120 | 12/1977 | Krapcho et al. | 514/210 |
| 4,115,382 | 9/1978 | Krapcho et al. | 544/111 |
| 4,166,907 | 9/1979 | Krapcho et al. | 544/111 |
| 4,174,317 | 11/1979 | Krapcho | 544/359 |
| 4,260,743 | 4/1981 | Bose | 546/275 |
| 4,510,086 | 4/1985 | Ross et al. | 540/360 |
| 4,534,896 | 8/1985 | Treuner et al. | 514/210 |
| 4,559,335 | 12/1985 | Zahler | 546/275 |
| 4,576,749 | 3/1986 | Zahler et al. | 544/311 |
| 4,680,391 | 7/1987 | Firestone et al. | 540/355 |
| 5,104,862 | 4/1992 | Durette | 540/360 |

FOREIGN PATENT DOCUMENTS

| | | |
|---|---|---|
| 295547 | 1/1972 | Austria . |
| 375640 | 8/1984 | Austria . |
| 0023097 | 1/1981 | European Pat. Off. . |
| 0042026 | 12/1981 | European Pat. Off. . |
| 0076621 | 4/1983 | European Pat. Off. . |
| 0199630 | 10/1986 | European Pat. Off. . |
| 0337549 | 10/1989 | European Pat. Off. . |
| 1945542 | 3/1971 | Fed. Rep. of Germany . |
| 2046822 | 3/1972 | Fed. Rep. of Germany . |
| 2046823 | 3/1972 | Fed. Rep. of Germany . |
| 2748827 | 5/1978 | Fed. Rep. of Germany . |
| 2824554 | 12/1978 | Fed. Rep. of Germany . |
| 2842466 | 4/1979 | Fed. Rep. of Germany . |
| 2911589 | 9/1979 | Fed. Rep. of Germany . |
| 3007298 | 9/1981 | Fed. Rep. of Germany . |
| 1192952 | 5/1970 | United Kingdom . |
| 1604752 | 12/1981 | United Kingdom . |
| 2093839 | 9/1982 | United Kingdom . |

OTHER PUBLICATIONS

Chem Abstracts, vol. 105, Abs. 97895t (1986).
Peitsch, Hartmut, Tetrahedron Letters No. 45, pp. 4053–4056 (1976).
Tanaka, et al Heterocycles vol. 24, No. 9, pp. 2539–2543 (1986).

*Primary Examiner*—M. L. Berch
*Attorney, Agent, or Firm*—Curtis C. Panzer; Raymond M. Speer

[57] ABSTRACT

Disclosed are β-lactams of formula I

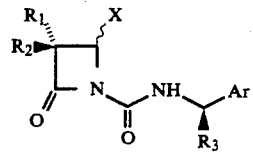

wherein X is a chromogenic or fluorogenic substituted aryl or heteroaryl, which are specific inhibitors of Human leukocyte elastase (HLE). Upon contact with HLE these compounds are cleaved to form a chromogenic or fluorogenic species which may be readily measured by the assay disclosed herein. The assay thus provides a means for direct measurement of the amount of active HLE in a body fluid or other sample.

4 Claims, No Drawings

β-LACTAMS USEFUL IN DETERMINING THE AMOUNT OF ELASTASE IN A CLINICAL SAMPLE

This application is a continuation in part of U.S. Ser. No. 761,191 filed Sep. 20, 1991 which is a continuation in part of Ser. No. 719,653, filed Jun. 12, 1991 (abandoned) and a continuation in part of Ser. No. 735,696 filed Jul. 25, 1991 (abandoned).

Ser. No. 719,653 is a continuation of Ser. No. 608,607 filed Oct. 31, 1990 (abandoned), which is a continuation of Ser. No. 388,771 filed Aug. 2, 1989 (abandoned), which is a continuation in part of Ser. No. 179,688 filed Apr. 11, 1988 (abandoned) which is a continuation in part of Ser. No. 089,797 filed Aug. 27, 1987 (abandoned) which is a continuation of Ser. No. 842,834 filed Mar. 27, 1986 (abandoned) which is a continuation in part of Ser. No. 721,811 filed Apr. 10, 1985 (U.S. Pat. No. 4,680,391) which is a continuation in part of Ser. No. 557,030 filed Dec. 1, 1983 (abandoned).

Ser. No. 735,696 is a continuation of Ser. No. 597,617 filed Oct. 15, 1990 (abandoned).

BACKGROUND OF THE INVENTION

The invention concerns compounds useful in determing the amount of active human leucocyte elastase in a body fluid or other sample. Human leucocyte elastase (HLE) is a therapeutic target implicated in a number of chronic inflammatory dieseases characterized by extensive destruction of proteinaceous components of structural tissue. These include inflammatory conditions resulting in connective tissue destruction, e.g., rheumatoid arthritis, emphysema, bronchial inflammation, osteoarthritis, spondylitis, lupus, psoriasis atherosclerosis, sepsis, septicemia, shock, periodontitis, cystic fibrosis, acute respiratory distress syndrome, and reperfusion injury. High levels of active HLE are found in the sputa samples from patients with cystic fibrosis and chronic bronchitis (ref). Irreversible inhibitors of HLE are believed to be useful therapeutic agents and should decrease the concentration of active elastase in the biological fluids of patients. See (Davies, P., (1991) Annals of the New York Academy of Sciences, ed. Weinbaum Giles and Krell, vol 624, pp 219-229).

The concentration of elastase in biological samples can be determined by immunological techniques (ref) although this will not necessarily distinguish between active and inactive enzyme. Active HLE can be measured in terms of its ability to hydrolyse a given substrate. However, this technique could result in underestimating the concentration of active elastase due to the presence of endogenous substrates or reversible inhibitors. In particular, HLE found in human sputa samples may be tightly complexed to the reversible inhibitor bronchial antileucoprotease (ALP, Gauthier, F., Fryksmark, U., Ohlsson, K., and Bieth, J. G. (1982) Biochim. et Biophys. Acta 700, 178-183). Irreversible active site titrants that utilize the catalytic machinary of the enzyme, require active enzyme and would be ideal for this purpose. Ideal active site titrants react specifically, rapidly, and stoichiometrically with the target enzymes. In addition irreversible active site titrants should produce stable enzyme-inhibitor complexes. Prior active reagents that meet these criteria are radiometric (e.g., radiolabeled diisopropylfluorophosphate as disclosure by Cohen, J. A., Oosterbann, R. A.,. and Berends, F., Methods Enzymol. 11, 81). Unfortunately, this reagent not only reacts with serine proteases but serine esterases as well. Initial active site titrants of serine proteases were often nonspecific. For example, 4-nitrophenyl-4-guanidinobenzoate developed for trypsin-like proteases also reacts with chymotrypsin (Chase, T. and Shaw, E. (1970) Methods Enzymol. 19, 20-27). More recently Gupton et al. (1984) and Powers et al. have pioneered the use of aza-peptides as active site titrants of serine proteases (see Gupton, B. F., Carroll, D. L., Tuhy, P. M., Kam, C-M., and Powers, J. C. (1984) J. Biol. Chem. 259, 4279-4287; and Powers, J. C. and Carroll, D. L. (1975) Biochem. Biophys. Res. Commun. 67, 639). For a review of this class of inhibitors see Powers, J. C. and Gupta, B. F. Methods Enzymol. 46, 208-216. The specificity can be controlled by the peptide sequence. While they are more specific, a reagent such as Z-Ala-Ala-Pro-Aala-ONp originally developed for elastase also reacts with chymotrypsin and subtilisin (Powers and Carroll, 1975). In addition, these reagents may react with nonspecific esterases or be degraded by other proteases found in biological samples. These reagents also form relatively labile enzyme-inhibitor complexes with half-lives of approximately 1 hour at 25° C. (ref). Aprotinin derivatives described by Mehlich et al. (1988) fare somewhat better in that they produce complexes with half-lives an order of magnitude more stable but the reagents are proteins (58 amino residues) and thus less practical to work with due to cost (Melich, A., Beckmann, J., Wenxel, H. R., and Tschesche, H. (1988) BBA 957, 420-429. Powers, J. C. Boone, R., Carroll, D. L., Gupton, B. F., Kam, C-M., Nishino, N., Sakamoto, M., and Tuhy, P. M. (1984) J. Biol. Chem. 4288-4294.)

SUMMARY OF THE INVENTION

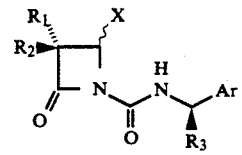

Disclosed are β-lactams of formula I which are specific inhibitors of Human leucocyte elastase (HLE). Upon contact with HLE these compounds are cleaved to form a chromogenic or fluorogenic species and thus provide a means for direct measurement of the amount of active HLE in a body fluid or other sample.

DETAILED DESCRIPTION OF THE INVENTION

In one embodiment the invention concerns compounds of formula I

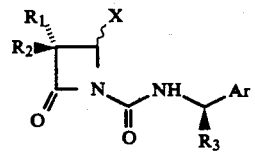

wherein
$R_1$ $R_2$ and $R_3$ are each independently selected from the group consisting of
  (a) H, and
  (b) methyl, ethyl and n—$C_3H_7$;
Ar is selected from the group consisting of
  (a) phenyl,
  (b) pyridyl, (c) pyrryl,
(d) thienyl,
(e) isothiazolyl,
(f) imidazolyl,
(g) tetrazolyl,
(h) pyrazinyl,
(i) pyrimidyl,
(j) quinolyl,
(k) isoquinolyl,
(l) benzothienyl,
(m) benzofuranyl,
(n) pyrazolyl,
(o) indolyl,
(p) purinyl,
(q) carbozolyl, and
(r) isoxazolyl;
or mono or di substituted Ar wherein the substituent is:
(a) H,
(b) $C_{1-3}$ alkyl,
(c) $C_{1-3}$ alkoxy, or
(d) halo;
X is selected from the group consisting of
(a)

[structure: phenol with $R_5$ and two $NO_2$ groups; or phenol with $NO_2$ and $R_5$]

wherein
$R_5$ is
(1) H,
(2) $CO_2H$, or
(3) $CH_2CO_2H$;
(b)

[structure: chromone-like with $R_6$, $R_7$, $R_8$ substituents]

wherein $R_6$ and $R_7$ are each independently selected from the group consisting of
(1) H, and
(2) $C_{1-3}$ alkyl;
and $R_8$ is
(1) H,
(2) $C_{1-3}$ alkyl,
(3) CN, or
(4) $CO_2H$;
(c)

[structure: phenoxazine N-oxide type]

wherein n is o or 1;
(d)

[structure: 4-thiopyridyl or 2-thiopyridyl]

(e)

[structure: stilbazolium, 4-hydroxystyryl-N-methylpyridinium] I or
(f)

[structure: fluorescein-type xanthene with $R_9$, $R_{10}$, $CO_2Na$]

wherein
$R_9$ is
(1) O,
(2) $NH_2^+$, or
(3) $N(CH_3)_2^+$; and
$R_{10}$ is
(1) H,
(2) $CO_2H$,
(3) $CO_2(C_1-C_3)$alkyl,
(4) $C_1-C_3$ alkyl,
(5) pyridyl,
(6) pyrryl,
(7) thienyl,
(8) isothiazolyl,
(9) imidazolyl,
(10) tetrazolyl,
(11) pyrazinyl,
(12) pyrimidyl,
(13) quinolyl,
(14) isoquinolyl,
(15) benzothienyl,
(16) isobenzofuryl,
(17) pyrazolyl,
(18) indolyl,
(19) purinyl,
(20) carbozolyl, or
(21) isoxazolyl.

As appreciated by those of skill in the art, the invention concerns the use of any counter ion such as a halide or sulfate.

One genus of this embodiment concerns the compounds wherein:
$R_1$ and $R_2$ are each ethyl and
$R_3$ is ethyl or n-propyl.

Within this genus is the class of compounds wherein:
Ar is mono substituted phenyl or substituted benzofuranyl.

Within this class is the subclass of compounds wherein X is selected from the group consisting of

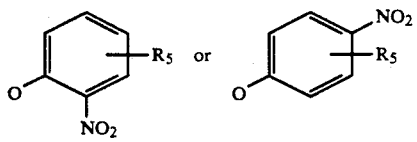

wherein
$R_5$ is
  (1) H,
  (2) $CO_2H$, and
  (3) $CH_2CO_2H$.

Illustrating the invention:
(a) (3,3-Diethyl-2(R,S)-(4-nitrophenoxy)-4-oxy-N-(phenylmethyl)-1-azetidinecarboxamide; and
(b) 4-(3,3-Diethyl-4-oxo-1-((1(R)-phenyl-n-propyl)aminocarbonyl)-2(R,S)-azetidinyl)oxy-3-nitrobenzeneacetic acid.

Further illustrating the invention are:
(a) 4-(3,3-Diethyl-4-oxo-1-((1(R)-phenyl-n-propyl)aminocarbonyl)-2(R)-azetidinyl)oxy-3-nitrobenzeneacetic acid; and.
(b) 4-(3,3-Diethyl-4-oxo-1-((1(R)-phenyl-n-propyl)aminocarbonyl)-2(S)-azetidinyl)oxy-3-nitrobenzeneacetic acid.

These compounds as active site titrants have several advantages over the previously reported classes of compounds. The stability of the compounds can be controlled due to the heavily substituted $\beta$-lactam ring. For example compound A of Example 1 compound was stable at pH 7.5 over an hour. The compounds are easy to use and the product chromophores can be detected in the presence of parent compound. The $\beta$-lactam derived enzyme-inhibitor complexes produced are stable.

A second embodiment concerns a method using compounds of Formula I:

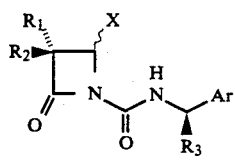

I for determining the human leucocyte elastase activity in a sample comprising:
(a) adding, in aqueous solution, in any order,
  (1) a compound of formula I,
  (2) human leucocyte elastase containing sample; and,
(b) measuring the human leucocyte elastase activity of the product of step (a) by photometric means, $R_1$ $R_2$ and $R_3$ are each independently selected from the group consisting of
(a) H, and
(b) methyl, ethyl and n-$C_3H_7$;
Ar is selected from the group consisting of
(a) phenyl,
(b) pyridyl,
(c) pyrryl,
(d) thienyl,
(e) isothiazolyl,
(f) imidazolyl,
(g) tetrazolyl,
(h) pyrazinyl,
(i) pyrimidyl,
(j) quinolyl,
(k) isoquinolyl,
(l) benzothienyl,
(m) benzofuranyl,
(n) pyrazolyl,
(o) indolyl,
(p) purinyl,
(q) carbozolyl, and
(r) isoxazolyl;
or mono or di substituted Ar wherein the substituent is:
(a) H,
(b) $C_{1-3}$ alkyl,
(c) $C_{1-3}$ alkoxy, or
(d) halo;
X is selected from the group consisting of
(a)

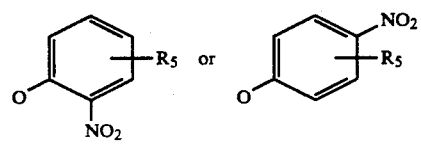

wherein
$R_5$ is
  (1) H,
  (2) $CO_2H$, or
  (3) $CH_2CO_2H$;
(b)

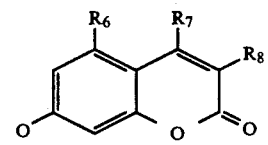

wherein $R_6$ and $R_7$ are each independently selected from the group consisting of
(1) H, and
(2) $C_{1-3}$ alkyl;
and $R_8$ is
(1) H,
(2) $C_{1-3}$ alkyl,
(3) CN, or
(4) $CO_2H$;
(c)

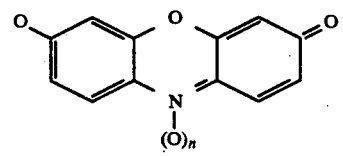

wherein n is 0 or 1;
(d)

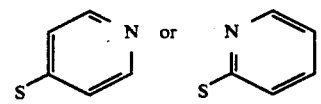

(e)

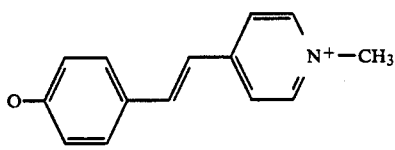

and (f)

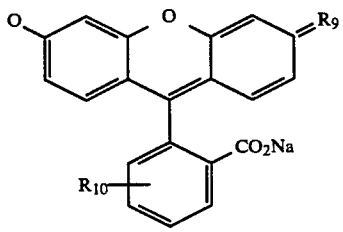

wherein
$R_9$ is
(1) O,
(2) $NH_2^+$, or
(3) $N(CH_3)_2^+$; and
$R_{10}$ is
(1) H,
(2) $CO_2H$,
(3) $CO_2(C_1-C_3)$alkyl,
(4) $C_1-C_3$ alkyl,
(5) pyridyl,
(6) pyrryl,
(7) thienyl,
(8) isothiazolyl,
(9) imidazolyl,
(10) tetrazolyl,
(11) pyrazinyl,
(12) pyrimidyl,
(13) quinolyl,
(14) isoquinolyl,
(15) benzothienyl,
(16) isobenzofuryl,
(17) pyrazolyl,
(18) indolyl,
(19) purinyl,
(20) carbozolyl, or
(21) isoxazolyl.

The above mentioned elastase containing sample, may be either a known elastase reference sample or an unknown sample such as sputum or other body fluid which contains elastase.

One genus of this embodiment concerns the compounds wherein:
$R_1$ and $R_2$ are each ethyl and
$R_3$ is ethyl or n-propyl.

Within this genus the invention concerns the use of compounds of Formula I wherein: Ar is substituted phenyl or substituted benzofuranyl.

Within this class is the subclass which concerns the use of compounds of Formula I wherein X is selected from the group consisting of

I

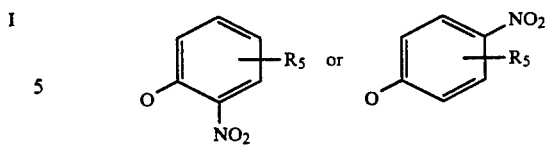

wherein
$R_5$ is
(1) H,
(2) $CO_2H$, and
(3) $CH_2CO_2H$.

Illustrating the invention is the use of:
(a) (3,3-Diethyl-2(R,S)-(4-nitrophenoxy)-4-oxy-N-(phenylmethyl)-1-azetidinecarboxamide; and
(b) 4-(3,3-Diethyl-4-oxo-1-((1(R)-phenyl-n-propyl)aminocarbonyl)-2(R,S)-azetidinyl)oxy-3-nitrobenzeneacetic acid.

Further illustrating the invention is the use of:
(a) 4-(3,3-Diethyl-4-oxo-1-((1(R)-phenyl-n-propyl)aminocarbonyl)-2(R)-azetidinyl)oxy-3-nitrobenzeneacetic acid; and
(b) 4-(3,3-Diethyl-4-oxo-1-((1(R)-phenyl-n-propyl)aminocarbonyl)-2(S)-azetidinyl)oxy-3-nitrobenzeneacetic acid.

The useful concentration of compound of Formula I in aqueous solution is down to 1 pM; or as shown in the Examples 1 μM to 10 mM. Typically, stock solutions are prepared in an organic solvent, such as DMSO, ethanol or isopropanol and diluted at least 20-fold in aqueous solution to achieve the desired concentration of inhibitor in the reaction mixture. The enzyme tolerates concentrations of some organic solvents (ethanol, isopropanol, DMSO) up to 20% (vol/vol) with no significant loss of enzyme activity. The choice of solvent is dictated entirely by the concentration desired in the assay, and the solubility of the inhibitor. Alternatively, the inhibitor stock solution can be prepared in buffer at a dilute concentration, and comprise a large percentage of the final reaction mixture.

Similarly, it is preferred that the aqueous solution comprises a buffer.

The pH optimum for HLE is between 6.5 and 8.0. Consequently, suitable buffer will have a pKa between 6.5 and 7.5, such as HEPES or TES, the latter which we used in our studies. In general, any nonreactive buffer at a concentration that will maintain the pH of the reaction between 6 and 9 will work.

Other components may be added to the reaction that stabilize the enzyme or increase the rate of the reaction. Examples are sucrose (such as 10%), CHAPS (such as 0.1%), DTT (1-100 mM), BSA (such as 0.1-10 mg/ml) and NaCl (typically 100-1100 mM) all of which have been demonstrated to stabilize certain enzymes. Others components which may be included are glycerol, EDTA.

The concentration of HLE is highly variable and may range from 1 pM to 1 μM, depending entirely on the purpose of a particular experiment. The volume added to a particular reaction may be very small or comprise the entire volume of the reaction less the volume of substrate required to achieve the desired concentration.

Enzyme for use in the method may be obtained from any cell capable of secreting HLE including but not limited to. Any state of purity of HLE is acceptable (including crude cell lysates).

The sample will typically comprise either, a putative HLE inhibitor or other modulator of HLE activity, in a concentration of 1 pM to 1M.

The assay is typically run between 25 and 37 degrees centigrade. The use of higher temperatures will depend upon the stability of the enzyme and running the assay at low temperatures will probably be dictated by practical considerations.

As appreciated by those of skill in the art, addition step (a) results in the cleavage of compound of formula I between the azetidinone described, and the substituent X. The liberation of the chromophoric group, X may be monitored by spectrophotometric or fluorometric procedures.

The method of detection will depend upon the chromophore released upon hydrolysis of X. Fluorometric leaving groups (e.g. AMC) require spectrofluorometer such as the Gilford Fluoro IV. The emission and excitation wavelengths will be selected based on the emission and excitation spectra of the substrate and product chromophore.

Inhibitors with spectrophotometric leaving groups (e.g. pNA) will require a spectrophotometer such as CARY 210 spectrophotometer. In this case the reaction will be monitored at a wavelength whose selection will be based on the absorbance spectra of the substrate and product chromophore. In the case of 4 hydroxy-3-nitrophenyl acetic acid (4HNPA) the wavelength selected is 428 nm, although this can vary appreciably with only a minor compromise in the sensitivity of the assay.

In general, the fluorometric assays will be at least 10-fold more sensitive than spectrophotometric assays, consequently, the fluorometric assay is preferred where enzyme concentration is low in the sample (e.g., μM or lower). However, in the event that large concentration the spectrophotometric assays are preferred. This assay is amendable to continuous or discontinuous sample of the reaction. The assay is also amenable to 96-well plate format for running multiple assays simultaneously.

Compounds of the instant invention are conveniently prepared using the procedures described generally below and more explicitly described in the Example section thereafter.

SCHEME 2

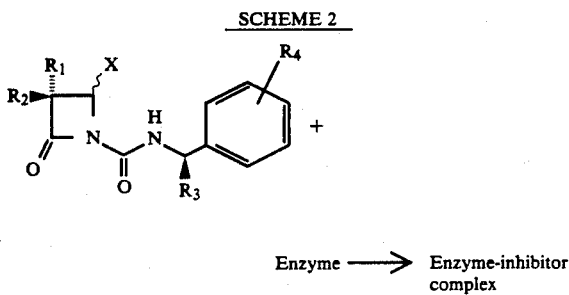

Enzyme ⟶ Enzyme-inhibitor complex

-continued
SCHEME 2

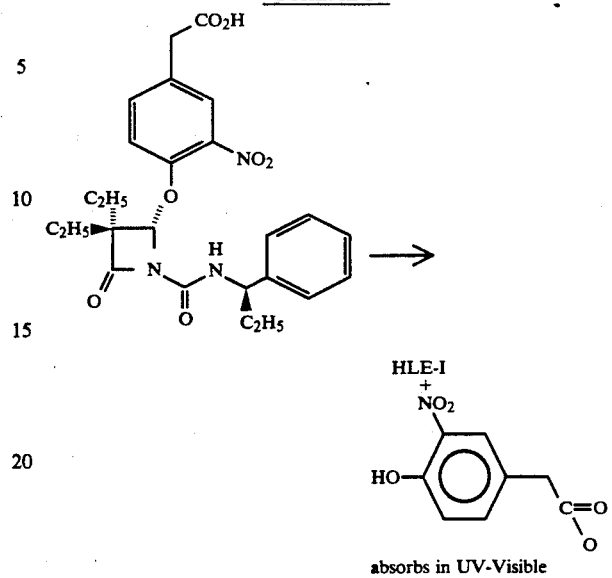

absorbs in UV-Visible

The following Examples are intended to illustrate the preparation of compounds of formula I, and as such are not intended to limit the invention as set forth in the claims appended thereto. Starting materials are either readily available or their method of Preparation known.

EXAMPLE 1

4-(3,3-Diethyl-4-oxo-1-((1(R)-phenyl-n-propyl-)aminocarbonyl)-2(R,S)-azetidinyl)oxy-3-nitrobenzeneacetic acid

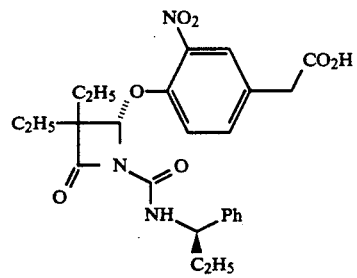

(a) 4-Hydroxy-3-nitrobenzene-acetic acid

Fuming nitric acid (1.36 mL) was slowly added to an ice cooled solution of 4-hydroxy-benzeneacetic acid (4.00 gm, 26.3 mmol) in acetic acid (25 mL). The yellow solution was allowed to warm to room temperature over an hour as a brown precipitant formed. The solid was filtered and recrystallized from ethyl acetate/hexanes as yellow needles (3.61 gm, 70% yield): $^1$H-NMR δ (CDCl$_3$-d$_4$DMSO, 4:1) 3.50 (2H, s), 7.04 (1H, d, J=9 Hz), 7.46 (1H, dd, J=9, 3 Hz), 7.94 (1H, d, J=3 Hz).

(b) t-Butyl 4-hydroxy-3-nitrobenzene-acetate 0-t-Butyl-N,N-diisopropyl-isourea (3.65 gm, 20 mmol) was added to a solution of 4-hydroxy-3-nitrobenzene-acetic acid (3.61 gm, 18.3 mmol) in t-butanol (18 mL) and stirred for 24 hours. Ethyl acetate (100 mL) was added and the solution washed successively with water 3×25 mL), 1N sodium bicarbonate solution 3×25 mL), and saturated salt solution (25 mL). The product was isolated as a yellow oil (1.02 gm, 22% yield) and used without further purification: $^1$H-NMR δ

(CDCl₃) 1.44 (9H, s), 3.52 (2H, s), 7.08 (2H, d, J=8 Hz), 7.51 (1H, dd, J=8, 3 Hz), 8.00 (1H, d, J=3 Hz).

(c) t-Butyl 4-(3,3-diethyl-4-oxo-2-(R,S)-azetidinyl) oxy-3-nitrobenzene-acetate

A solution of 2-acetoxy-3,3-diethyl-4-oxo-azetidine (0.75 gm, 4.1 mmol) in acetone (3 mL) was added to an ice cooled solution of t-butyl 4-hydroxy-3-nitrobenzene-acetate (1.02 gm, 4.0 mmol) in 2.0N sodium hydroxide (2 mL). After stirring at room temperature for 4 hours, ethyl acetate (75 mL) was added and the solution washed successively with water (3×20 mL) and saturated salt solution (20 mL). The solution was dried over anhydrous sodium sulfate and the solvent rotoevaporated. The product was purified by flash column chromatography on silica gel eluted with 35% ethyl acetate in hexanes and isolated as a colorless oil (0.96 gm, 63% yield): ¹H-NMR δ (CDCl₃) 0.95 (3H, t, J=7 Hz), 0.99 (3H, t, J=7 Hz), 1.40 (9H, s), 1.52-2.00 (4H, m), 3.49 (2H, s), 5.35 (1H, s), 6.93 (1H, d, J=9 Hz), 7.44 (1H, dd, J=9, 3 Hz), 7.50 (1H, s), 7.74 (1H, d, J=3 Hz).

(d) t-Butyl 4-(3,3-diethyl-4-oxo-1-(1(R)-phenyl-n-propylaminocarbonyl)-2-(R)-acetidinyl)oxy-3-nitrobenzene-acetate, and 4-(3,3-diethyl-4-oxo-1-(1(R)-phenyl-n-propylaminocarbonyl(-2-(S)-azetidinyl) oxy-3-nitrobenzene-acetate.

Triethylamine (0.70 mL, 5.0 mmol), 4-dimethylaminopyridine (20 mg, 0.1 mmol), and 1(R)-phenylpropyl isocyanate (0.6 gm, 3.8 mmol) were successively added to a solution of t-butyl 4-(3,3-diethyl-4-oxo-2-azetidinyl)oxy-3-nitrobenzene-acetate (0.96 gm, 2.5 mmol) in methylene chloride (5 mL). The solution was stirred at room temperature for 3 hours, then ethyl acetate (50 mL) was added. The solution was successively washed with 1N hydrochloric acid (3×10 mL), 1N sodium bicarbonate solution (3×10 mL), water (20 mL), and saturated salt solution (10 mL). The solution was dried over anhydrous sodium sulfate and the solvent removed by rotoevaporation. The products were purified by flash column chromatography on silica gel eluted with 15% ethyl acetate in hexanes and isolated as clear oils: first eluted isomer A (275 mg, 20% yield) ¹H-NMR δ (CDCl₃) 0.89 (3H, t, J=7 Hz), 0.92 (3H, t, J=7 Hz), 1.05 (3H, t, J=8 Hz), 1.43 (9H, s), 1.72-1.95 (5H, m), 1.96-2.14 (1H, m) 3.51 (2H, s), 4.74 (1H, q, J=8 Hz), 5.63 (1H, s), 6.98 (1H, d, J=8 Hz), 7.23-7.31 (5H, m), 7.42 (1H, dd, J=8 Hz), 7.73 (1H, d, J=2 Hz), 7.84 (1H, d, J=8 Hz); second eluted isomer B (331 mg, 24% yield) ¹H-NMR δ (CDCl₃) 0.88 (3H, t, J=7 Hz), 1.02 (3H, t, J=7 Hz), 1.06 (3H, t, J=7 Hz), 1.43 (9H, s), 1.76-1.95 (5H, m), 1.98-2.05 (1H, m), 3.49 (2H, s), 4.79 (1H, q, J=7 Hz), 5.69 (1H, s), 6.96 (1H, d, J=7 Hz), 7.20-7.35 (5H, m), 7.44 (1H, dd, J=8, 2 hz), 7.70 (1H, d, J=2 Hz), 7.84 (1H, d, J=8 Hz).

(e) 4-(3,3-diethyl-4-oxo-1-(1(R)-phenyl-n-propylaminocarbonyl)-2-(R)-acetidinyl)oxy-3-nitrobenzene-acetic acid, and 4-(3,3-diethyl-4-oxo-1-(1(R)-phenyl-n-propylaminocarbonyl)-2-(S)-acetidinyl)oxy-3-nitrobenzene-acetic acid.

Trifluoroacetic acid (2 mL) was added to a solution of the first eluted isomer A from (d) (275 mg, 0.5 mmol) in anisole (0.5 mL) at 0° C. After stirring at 0° C. for 6 hours, methylene chloride (2 mL) was added and the solvent removed by rotoevaporated under high vacuum. The product was purified by flash column chromatography on silica gel eluted with 1% acetic acid in 25% ethyl acetate/hexanes and was isolated as a clear foam (193 mg, 78% yield): ¹H-NMR δ (CDCl₃) 0.89 (3H, t, J=7 Hz), 0.93 (3H, t, J=7 Hz), 1.05 (3H, t, J=7 Hz), 1.65-1.83 (5H, m), 1.90-2.05 (1H, m), 3.63 (2H, s), 4.74 (1H, q, J=8 hz), 5.64 (1H, s), 7.00 (1H, d, J=8 Hz), 7.22-7.34 (5H, m), 7.45 (1H, dd, J=8, 2 hz), 7.73 (1H, d, J=2 hz); ir (thin film) 1780, 1700 cm⁻¹.

Chem. anal. Calc. C, 62.10; H, 6.05; N, 8.69. Fd. C, 61.90; H, 6.24; N, 8.42.

The lower isomer B from (d) was treated accordingly and was also obtained as a clear foam in 78% yield: 1H-NMR d (CDCl3) 0.89 (3H, t, J=7 hz), 0.99 (3H, t, J=7 Hz), 0.99 (3H, t, J=7 Hz), 1.03 (3H, t, J=7 Hz), 1.75-1.95 (5H, m), 1.96-2.10 (1H, m), 3.61 (2H, s), 4.95 (1H, q, J=8 Hz), 5.70 (1H, s), 6.98 (1H, d, J=8 hz), 7.25-7.39 (5H, m), 7.44 (1H, dd, J=8, 2 Hz), 7.70 (1H, d, J=2 Hz), 7.81 (1H, d, J=8 Hz); ir (thin film) 1780, 1709 cm⁻¹.

Chem. anal Calc. C, 62.10; H, 6.05; N, 8.69. Fd. C, 62.03; H, 6.16; N, 8.39.

EXAMPLE 2

Preparation of (3,3-Diethyl-2-(R,S)-(4-nitrophenoxy)-4-oxo-N-(phenyl methyl)-1-azetidinecarboxyamide (compound C)

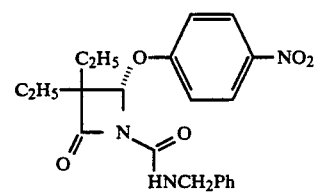

(a) 4-(3,3-Diethyl-4-oxo-2-(R,S)-azetidinyl)oxynitrobenzene

A solution of 4-nitrophenol (2.37 gm, 17.0 mmol) in 2.5N sodium hydroxide (6.82 mL) was added to a solution of 2-acetoxy-3,3-diethyl-4-oxoazetidine (1.05 gm, 5.7 mmol) in acetone (5 mL). After stirring at room temperature for 2.5 hours, ethyl acetate (100 mL) was added and the solution successively washed with water (3×20 mL) and saturated salt solution (20 mL). The solution was dried over anhydrous sodium sulfate and the solvent removed by rotoevaporated. The product was purified by flash column chromatography on silica gel eluted with 25% ethyl acetate in hexanes and isolated as a beige solid (1.20 gm, 80% yield): ¹H-NMR δ (CDCl₃) 0.94 (6H, t, J=7 Hz), 1.62-1.92 (4H, m), 5.38 (1H, s), 6.90 (2H, d, J=9 Hz), 7.66 (1H, s), 8.10 (2H, d, J=9 Hz).

(b) 4-(3,3-Diethyl-4-oxo-1-(phenylmethylaminocarbonyl)-2-(R, S)-azetidinyl)oxy-nitrobenzene Triethylamine (1.26 mL, 9.1 mmol), 4-dimethylaminopyridine (20 mg, 0.2 mmol), and benzyl isocyanate (1.12 mL, 9.1 mmol) were successively added to a solution of 4-(3,3-diethyl-4-oxo-2-azetidinyl)oxy-nitrobenzene (1.2 gm, 4.6 mmol) in methylene chloride (10 mL). The solution was stirred at room temperature for 1.5 hours, then ethyl acetate (100 mL) was added. The solution was sucessively washed with 1N hydrochloric acid (3×20 mL), 1N sodium bicarbonate solution (3×20 mL), water (20 mL), and saturated salt solution (20 mL), 1N sodium solution was dried over anhydrous sodium sulfate and the solvent removed by rotoevaporated. The product was purified by flash column chromatography on silica gel eluted with 15% ethyl acetate in hexanes and recrystallized from ethyl acetate/hexanes as a white solid (mp. 96°-97° C.; 1.3 gm, 70% yield): ¹H-NMR δ (CDCl₃) 1.04 (3H, t, J=7 hz), 1.08 (3H, t, J=7 Hz), 1.76–2.10 (4H, m), 4.47 (2H, d, J=6 hz), 5.76 (1H, s), 7.26–7.44 (7H, m), 8.24 (2H, d, J=9 Hz; ir (thin film) 1780, 1720 cm$^{-1}$.

Chem. anal.: Calc. C, 63.46; H, 5.83; N, 10.57. Fd. C, 63.43; H, 5.49; N, 10.49.

EXAMPLE 3

ASSAY: Inhibition of Human Leucocyte elastase (HLE) by Compound A

Enzyme: HLE was purchased from ELASTIN PRODUCTS.

Stock solutions were prepared containing from 1–4 mg/ml HLE in buffer A as defined below.

Substrate: 4-(3-Diethyl-4-oxo-1-(1R)-phenyl-n-propylaminocarbonyl)-2-(R)-azetidinyl)oxy-3-nitrobenzene-acetic acid (Compound A, Example 1). Stock solution was prepared containing 10 mM compound A in DMSO. The resulting stock solution is then diluted 1 to 10 with Buffer A.

Buffer A: 450 mM NaCl, 10% DMSO, and 45 mM TES buffer at pH 7.5.

From these diluted stock solutions, a solution was prepared containing 0.28 mM Compound A and 0.036 mM HLE. Liberation of 4-hydroxy-3-phenylacetic acid was then monitored on a VARIAN DMS 300 spectrophotometer at 428 nm. See Green et al., *Arch. Biochem. and Biophys.* 286, 284–292.

Results: The absorbance increased 0.139 O.D. This represents a value of 0.0397 nM or 1.1 equivalents of 4-hydroxy-3-nitrophenyl acetic. [4-hydroxy-3-nitrophenyl acetic acid was determined to have an extinction coefficient of 3,500 per M cam at a pH 7.5. ] Thus, 1 mole of HLE was found to liberate 1.1 mole of 4-hydroxy-3-nitrophenyl acetic acid.

It is to be noted that the actual concentration of HLE was determined by the method of Green et al, supra, using MeO-AAPV-pNA or Succ-AAPA-pNA purchased from CALBIOCHEMICAL COMPANY and CHEMICAL CYNAMICS, respectively.

EXAMPLE 3a

Using the same procedure with Compound C, 1 mole of HLE was found to liberate approximately 2.1 mole of 4-hydroxy-1-nitrophenylate.

EXAMPLE 4

Assay: Determination of HLE in sputum.

Enzyme: Solutions were prepared as shown in Example 3.

Substrate: Stock solution was prepared as shown in Example 3, but the diluted in DMSO rather than buffer A.

Sputum extract: Sputa samples are collected from human patients. The Sputa samples are extracted with 3 volumes of Phosphate buffered saline by shaking.

From the diluted stock solutions, a solution was prepared by addition of 0.58 ml of sputum extract, 0.5 ml of 0.073 mM HLE and 0.1 ml of 2.8 mM Compound A, resulting in final concentrations of 0.25 mM Compound A and 0.0332 mM HLE. Liberation of 4-hydroxy-3-nitrophenyl acetic acid was then monitored on a VARIAN DMS 300 spectrophotometer at 428 nm.

Results: The absorbance at 428 nm increased 0.116 O.D. corresponding to liberation of 0.33 mM of 4-hydroxy-3-nitrophenyl acetic acid. Based on the equivalency found in Example 3, the concentration of 0.033 mM HLE was determined.

What is claimed is:

1. A compound which is (3,3-Diethyl-(R,S)-(4-nitrophenoxy)-4-oxo-N-(phenylmethyl)-1-azetidinecarboxyamide.

2. A compound which is 4-(3,3-Diethyl-4-oxo-1-((1(R)-phenyl-n-propyl)aminocarbonyl)-2(R,S)-azetidinyl)oxy-3-nitrobenzeneacetic acid.

3. A compound which is 4-(3,3-Diethyl-4-oxo-1-((1(R)-phenyl-n-propyl)aminocarbonyl)-2(R)-azetidinyl)oxy-3-nitrobenzeneacetic acid; and.

4. A compound which is 4-(3,3-Diethyl-4-oxo-1-((1(R)-phenyl-n-propyl)aminocarbonyl-2(S)-azetidinyl)oxy-3-nitrobenzeneacetic acid.

* * * * *